United States Patent [19]

Harp

[11] Patent Number: 5,362,650
[45] Date of Patent: Nov. 8, 1994

[54] ULTRA-LOW RANGE CHLORINE DETERMINATION

[75] Inventor: Daniel L. Harp, Loveland, Colo.

[73] Assignee: Hach Company, Loveland, Colo.

[21] Appl. No.: 131,140

[22] Filed: Oct. 4, 1993

[51] Int. Cl.$^5$ ............................................. G01N 31/12
[52] U.S. Cl. ..................................... 436/125; 436/177
[58] Field of Search ................ 436/125, 164, 171, 177

[56] References Cited

U.S. PATENT DOCUMENTS

| | | | |
|---|---|---|---|
| 3,811,840 | 5/1974 | Bauer et al. | 436/129 X |
| 4,234,316 | 11/1980 | Hevey | 436/166 |

FOREIGN PATENT DOCUMENTS

| | | | |
|---|---|---|---|
| 489483 | 1/1953 | Canada | 436/125 |
| 1218942 | 9/1986 | Japan . | |
| 3211565 | 8/1988 | Japan | 436/125 |
| 1223345 | 9/1989 | Japan | 436/125 |
| 813493 | 5/1959 | United Kingdom | 436/125 |
| 1053184 | 1/1967 | United Kingdom | 436/125 |

OTHER PUBLICATIONS

Patrovsky, "Photometric determination of free chlorine . . . " *Chemistry*, 80(12), 1986, 1297—1301.

Wang et al. "Improvement of DPD colorimetry for the determination . . . " *Huanjing Kexune*, 7(1), 74–6, 1986.

*Primary Examiner*—Robert J. Warden
*Assistant Examiner*—Robert Carpenter
*Attorney, Agent, or Firm*—Dean P. Edmundson

[57] ABSTRACT

A method for determining trace amounts of total chlorine present in a water sample. The method includes use of DPD as an indicator. The sample is filtered after a color development delay, and then light absorbance through the sample is measured. A control sample is treated with malonic acid to de-chlorinate the control. Light absorbance through the sample being tested is adjusted by the light absorbance through the control sample.

7 Claims, 1 Drawing Sheet

ULTRA-LOW RANGE CHLORINE DETERMINATION

FIELD OF THE INVENTION

This invention relates to tests for determining the amount of chlorine present in water. More particularly, this invention relates to improvements to the reagents and procedure used for measuring trace chlorine in water, and a method for compensating for the amount of interference caused by the addition of the reagents (the reagent blank) in a chlorine test. Even more particularly, this invention relates to an effective ultra-low range chlorine test.

BACKGROUND OF THE INVENTION

Waste water treatment plants use chlorine for controlling various bacteria in water effluents. However, concern as to toxicity of chlorine and chlorine-containing chemicals in the effluent to aquatic organisms has resulted in pressure on operators of waste water treatment plants to reduce residual chlorine in waste water effluents discharged into natural waters.

The amount of residual chlorine permitted in water effluents varies from one facility to another. Normally the allowable amount of chlorine is typically less than about 100 micrograms per liter as "total" chlorine. Total chlorine is the terminology used to express chlorine which may exist in the free available form plus that which is combined with nitrogen compounds (chloramines). At some facilities the total chlorine level in discharged water must be less than 5 micrograms per liter. The amount of chlorine in the treated effluent must be monitored frequently by the waste water facility.

Historically, wastewater facilities have used probe detectors, such as those based on amperometric, potentiometric, or polarographic principles to analyze low chlorine levels present in their treated wastewater. One serious problem with these devices has been the fouling of the metal electrode or membrane surfaces that are in contact with the wastewater sample. The fouling can cause a drift of the electrode output or a diminished response which will result in errors in the measurement. These probe devices also require special operator skills to achieve accurate results below 50 micrograms per liter chlorine in wastewater analyses.

Colorimetric analytical methods for chlorine, such as those published in Standard Methods for the Examination of Water and Wastewaters, have only limited application for measuring trace chlorine levels in wastewaters. The colorimetric methods are limited by instability of the reagents formulated for the test, instability of the colored reaction product, and inadequate compensation for turbidity, color and particulate matter. In addition, the reagents added to the sample can cause a "reagent blank" due to impurities in the reagents, which may lead to serious errors at the trace measurement levels if not compensated for accurately.

There has not heretofore been provided an effective ultra-low range test for chlorine determination in wastewater at levels below 50 µg/liter.

SUMMARY OF THE INVENTION

In accordance with the present invention there is provided an improved method for determination of ultra-low amounts (e.g., detection down to 2 micrograms per liter) of chlorine in water. The method involves the use of the N,N-diethyl-p-phenylenediamine (DPD) indicator.

Although the use of DPD as an indicator for chlorine in water has been previously published, a stable liquid DPD indicator reagent has not been reported. Control of the DPD indicator stability is important in the function of the ultralow range chlorine test. Instability of the indicator will result in less sensitivity of the indicator to chlorine (i.e., the sensitivity diminishes over time). Also, oxidation of the DPD indicator, due to exposure to the atmosphere or to oxygen dissolved in the preparation water, will result in a reagent blank, which will interfere in the analytical test.

The stability of the DPD indicator is affected by several factors which have not been adequately addressed in the published formulations. These factors are related to oxidation of the DPD indicator which is a function of solution acidity. In the present invention these factors have been investigated and controlled, resulting in a DPD indicator reagent solution which exhibits increased stability (over one year shelf life) and provides a low and consistent reagent blank.

The test for chlorine in water requires buffering of the sample between a pH of 6.0–6.7. Buffer reagent solutions cited in the literature are not adequate for testing ultra-low levels of chlorine in wastewaters. Impurities in the buffer reagent components can cause a reagent blank or may exert a "chlorine demand". The chlorine demand may consume chlorine in the water sample yielding a low analytical result. Over time, potassium iodide, which is added to the buffer or to the sample separately to include chloramines in the test results, can be oxidized to free iodine or iodate, which react directly with the DPD indicator.

By producing the buffer/iodide reagent solution with pure materials, controlled for chlorine demand and oxidants, and by protecting the reagent from oxidation, a stable (over one year shelf life) buffer reagent solution can be prepared which exhibits no chlorine demand and minimum reagent blank value.

Combined reagent formulations of indicator and buffer are available commercially as relatively stable powders. However, these powders do not dissolve completely in the water sample and the remaining turbidity would interfere in colorimetric measurements below 50 µg/L chlorine.

Turbidity and particulate matter, frequently present in wastewater effluent samples, will interfere at the low color absorbance levels required for the chlorine test. Due to chlorine's relative instability and volatility in water, classical chemical separation techniques, such as prefiltration of the water sample to remove the suspended particles, will result in a loss of chlorine. A method has been developed to perform the filtration after the reaction of chlorine with the DPD indicator. The "post-filtration" operation utilizes an inert filter media which does not retain the DPD reaction product but adequately removes the interfering particulates from the sample.

The post-filtration apparatus (shown in FIG. 1) includes a syringe, syringe plunger, a membrane filter holder and the filter membrane. The pore size of the filter membrane is critical in terms of adequate removal of the sample particulate matter which can interfere at the wavelength selected for the test. However, a more restrictive porosity is to be avoided since this would lead to inability to filter an adequate volume of sample within the time constraint of the test. A filter porosity that excludes particles larger than 3 micrometers ($\mu m$) in diameter appears optimum for the ultralow range chlorine test.

The composition of the filter material is also critical for function of the test. The reaction product of DPD with chlorine is a relatively stable cationic (positive-charged) species. It is important in accurate quantification of chlorine in the sample that the cationic reaction product passes through the filter surface unhindered. The filter surface must not exhibit an electrostatic charge or be manufactured of materials prone to ionic charges. If the filter surface is charged, the cationic reaction product would be retained on the filter surface or repelled from the surface. Membrane filters manufactured from inert polymeric materials, such as acrylic polymers, linear polyethylenes, nylon or fluoridated polymers, function as adequate particulate barriers without inhibiting pass-through of the reaction product.

As cited previously, reagents added to the sample may result in an increase in color due to impurities in the reagents (a reagent blank). The reagent blank in the ultralow chlorine test would arise primarily from oxidation of the DPD indicator, resulting in a colored oxidation product identical to that obtained from the reaction of DPD with sample chlorine. Ideally, the reagent blank could be determined by use of a water sample that contained no oxidizing or reducing chemical compounds. Unfortunately, water that is completely void of oxidants or reductants is not readily available. Optionally, if chlorine and chloramines are removed from the water sample without affecting the reagent addition color, a reagent blank determination can be made.

A procedure to determine the reagent blank contribution has been developed that will remove chlorine and chloramines from the sample without affecting the color contributed by the DPD reagent. The sample is de-chlorinated by the addition of a malonic acid solution followed by the test procedure. The reagent blank value is subtracted from the test results, yielding a corrected sample total chlorine concentration.

By incorporating these improvements and techniques, it is possible to accurately determine levels of total chlorine in water down to 2 $\mu g$/liter. Other advantages of the invention will be apparent from the following detailed description.

BRIEF DESCRIPTION OF THE DRAWINGS

The invention is described in more detail hereinafter with reference to the accompanying drawing.

DETAILED DESCRIPTION OF THE INVENTION

Figure 1:
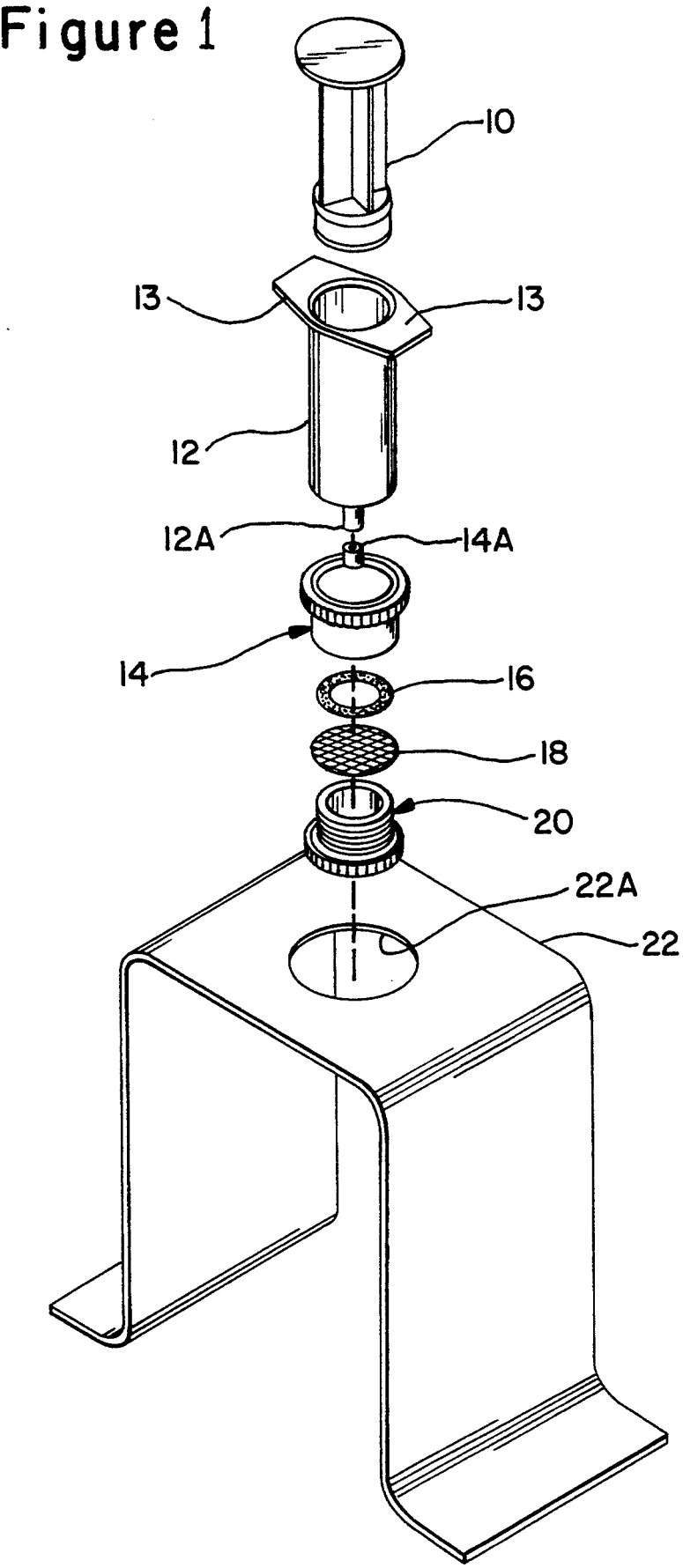
FIG. 1 is an explosion view showing a preferred embodiment of filtration apparatus useful in the present invention.

The present invention utilizes N,N-diethyl-p-phenylenediamine (DPD) as an indicator reagent solution. DPD is available commercially as the free base at various levels of purity. 1.6 grams of freshly distilled free base DPD is mixed into 1 liter of de-oxygenated 1 Normal sulfuric acid solution. The distillation is performed under vacuum to protect the DPD from oxidation. The mixing with acid is performed under an inert gas, such as argon, nitrogen or helium.

The DPD indicator may also be prepared from commercially available salts, such as N,N-diethyl-p-phenylenediamine oxalate, N,N-diethyl-p-phenylenediamine sulfate, or N,N-diethyl-p-phenylenediamine chloride. A calculated amount of the salt is added and dissolved into 1 liter of de-oxygenated 1 Normal sulfuric acid solution under an inert gas. Due to the possible oxidation of the intermediate, DPD indicator solutions prepared from the DPD salts tend to exhibit slightly higher reagent blanks.

The DPD indicator reagent solution is preferably packaged at a nominal volume into glass ampules, flushed with an inert gas. The filled ampules are flame-sealed under an inert gas. Other packaging techniques which exclude atmospheric oxygen may be utilized.

Buffer reagent solution is prepared, for example, by dissolving 123 grams sodium monohydrogen phosphate, 195 grams anhydrous sodium citrate, 117 grams potassium iodide, controlled for iodine, and 3 grams disodium EDTA in 600 milliliters (ml) deionized water. The solution is treated with powdered activated carbon between 40–50 degrees Celsius. The carbon is removed and the solution volume is adjusted to 1 liter. The buffer solution is packaged at a nominal volume into glass ampules, flushed with an inert gas. The filled ampules are flame-sealed under an inert gas. Other packaging techniques which exclude atmospheric oxygen may also be utilized.

Other citrate/phosphate buffer formulations which buffer the sample between a pH of 5–7 may be used provided these are treated to remove impurities that may exert a chlorine demand or contribute a reagent blank, and provided that they are protected from oxidation.

A blanking reagent is required for determination of the reagent blank value. The blanking reagent is prepared by dissolving 260 grams malonic acid in 0.7 liter deionized water. After filtering, the reagent volume is adjusted to 1 liter. The purpose of the blanking reagent is to remove all traces of free and combined forms of chlorine from the water sample or a surrogate. The concentration of malonic acid may vary depending on the relative concentration of chlorine/chloramine compounds to be removed and the sample volume.

The method of the invention involves opening one ampule each of DPD indicator and buffer reagents and transferring 1 ml of each to a suitable volumetric glassware. The reagents are swirled to mix. Water sample is added to the mixed reagents to a total volume of 50 ml and the solution is carefully mixed. Three minutes are allowed for reaction of DPD with the sample chlorine/chloramines. During the reaction period, at least 30 ml of the original water sample is filtered through the post-filtration apparatus shown in FIG. 1, containing a 3-micron porosity non-ionic membrane filter composed of an acrylic co-polymer or similar inert material. The filtered sample is poured into a fix-oriented flow cell (2.4 centimeter or greater) pathlength installed in a spectrophotometer, filter photometer or colorimeter set at a wavelength between 490–555 nanometers. The absorbance is set to zero with the filtered sample.

After the three minute reaction period, the reacted sample is filtered using the post-filtration apparatus through a 3-micron porosity membrane filter, composed of an acrylic co-polymer or suitable inert material. Within one minute of filtration, the filtered reacted sample is poured into the flow cell and the absorbance is measured. The absorbance value is due to the amount of total chlorine in the water sample plus the reagent blank. After correcting the absorbance for the reagent blank, the concentration of total chlorine is determined from a standard calibration graph.

The introduction of the protected reagents to sample or sample to reagents could vary depending on the instrumental technique used (e.g., flow injection analysis, process analyzer, segmented flow analysis, etc.).

The reagent blank is determined on a suitable sample of deionized or tap water which contains relatively low amounts of turbidity or particulate matter. Alternatively, the reagent blank can be determined on the water/wastewater sample being tested. The reagent blank is independent of the sample used. It is more convenient to use low-turbidity deionized or tap water to avoid the need for filtration.

To determine the reagent blank, 1 ml of the blanking reagent is added to 100 ml of low-turbidity water and the solution is mixed. Five minutes is allowed for full dechlorination. After de-chlorination, the test procedure for the ultra-low range DPD method is followed as outlined above. The absorbance obtained is due to the reagent blank. This value, typically equivalent to less than 5 µg/L chlorine, is used to correct the sample concentration result.

FIG. 1 illustrates a preferred form of filtration apparatus which is useful in the practice of this invention. The apparatus includes a plunger 10 which is adapted to slide into the open end of the barrel 12. At the lower end of the barrel there is a tip 12A which is adapted to fit into the tip 14A on the top of the upper section 14 of the filter holder. This is a friction fit so that the syringe can be easily coupled or de-coupled from the filter holder as needed. The lower portion 20 of the filter holder is adapted to threadably engage the upper portion 14 of the filter holder so as to retain the membrane filter 18 and an 0-ring 16 within the holder. The membrane filter may have a porosity in the range of about 1 to 5 microns, with a porosity of 3 microns being preferred.

The syringe barrel also includes outwardly projecting ears 13 so that the syringe barrel can be supported by the ears on the stand 22 when the main body of the syringe, and the filter holder, pass through the opening 22A at the top of stand. A beaker is normally positioned within the stand beneath the filter holder, and the sample to be filtered is poured into the open syringe barrel. Then, with the syringe being supported by ears 13 at the top of the stand, the plunger 10 is inserted into the syringe barrel and forced downwardly to force the water sample through the filter membrane and into the beaker.

Other variants are possible without departing from the scope of this invention.

What is claimed is:

1. A method for determining trace amounts of total chlorine in a sample of water, the method comprising the steps of:
    (a) adding a chlorine indicator to said sample, wherein said indicator comprises a liquid solution of N,N-diethyl-p-phenylenediamine;
    (b) adding a buffer reagent to said sample;
    (c) after a color development delay, filtering said sample;
    (d) measuring light absorbance of said sample; and
    (e) comparing said light absorbance with the absorbance of a control sample to which has been added a blanking reagent to de-chlorinate said control sample, wherein said blanking reagent comprises malonic acid.

2. A method in accordance with claim 1, wherein said buffer reagent is capable of adjusting the pH of said sample into the range of 6.0 to 6.7.

3. A method in accordance with claim 1, wherein said light absorbance is measured colorimetrically at 490–555 nm.

4. A method in accordance with claim 1, wherein said indicator is packaged in an oxygen-free container.

5. A method in accordance with claim 1, wherein said filtering step comprises passing said sample through an inert filter having a porosity of 3 microns.

6. A method in accordance with claim 1, wherein said buffer reagent is packaged in an oxygen-free container.

7. A method for determining trace amounts of total chlorine in a sample of water, the method comprising the steps of:
    (a) packaging a chlorine indicator in an oxygen-free container, wherein said indicator comprises a liquid solution of N,N-diethyl-p-phenylenediamine;
    (b) packaging a buffer reagent in an oxygen-free container;
    (c) adding said chlorine indicator to said sample;
    (d) adding said buffer reagent to said sample;
    (e) after a color development delay, filtering said sample through a non-ionic membrane filter;
    (f) measuring light absorbance of said sample;
    (g) comparing said light absorbance with the absorbance of a control water sample to which has been added said indicator and a blanking reagent to dechlorinate said control water sample, wherein said blanking reagent comprises malonic acid.

* * * * *